(12) United States Patent
Kawarai et al.

(10) Patent No.: US 8,562,910 B2
(45) Date of Patent: Oct. 22, 2013

(54) METHOD AND APPARATUS FOR ANALYSIS OF POLY (BIPHENYL CHLORIDE) IN ELECTRICAL INSULATING OIL

(75) Inventors: Masako Kawarai, Hitachinaka (JP); Junkichi Miura, Hitachi (JP); Tami Hiruta, Iwaki (JP); Yoshinori Inoue, Mitaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 119 days.

(21) Appl. No.: 12/994,300

(22) PCT Filed: May 20, 2009

(86) PCT No.: PCT/JP2009/059256
§ 371 (c)(1),
(2), (4) Date: Feb. 16, 2011

(87) PCT Pub. No.: WO2009/142232
PCT Pub. Date: Nov. 26, 2009

(65) Prior Publication Data
US 2011/0126609 A1 Jun. 2, 2011

(30) Foreign Application Priority Data

May 23, 2008 (JP) ................................. 2008-135013

(51) Int. Cl.
*G01N 30/02* (2006.01)
(52) U.S. Cl.
USPC ................ 422/70; 422/50; 422/68.1; 422/69; 210/634; 210/656; 210/660; 210/661; 210/663
(58) Field of Classification Search
USPC ............... 422/50, 68.1, 69, 70; 210/634, 656, 210/660, 661, 663
See application file for complete search history.

(56) References Cited

U.S. PATENT DOCUMENTS

2002/0004561 A1* 1/2002 Takahashi et al. ......... 525/326.9

FOREIGN PATENT DOCUMENTS

| JP | 04-059047 | 2/1992 |
|---|---|---|
| JP | 2000-088825 | 3/2000 |
| JP | 2001-083128 | 3/2001 |
| JP | 2002-365273 | 12/2002 |
| JP | 2006-313125 | 11/2006 |
| JP | 2009-281903 | 12/2009 |

OTHER PUBLICATIONS

Masako Kawarai, Introduction of sample Cleanup Method Using the Hitachi NOBIAS Series, S.I.News 2008, vol. 51, No. 2.
Testing method for polychlorobiphenyl in industrial water and wastewater, Japanese Industrial Standard, JIS K0093: 2002.

(Continued)

*Primary Examiner* — Monique Cole
(74) *Attorney, Agent, or Firm* — Antonelli, Terry, Stout & Kraus, LLP.

(57) ABSTRACT

An object of the present invention is to provide a method and an apparatus by which PCBs in insulating oil can be analyzed with high accuracy in a convenient, inexpensive, and rapid manner. The method for analyzing polychlorobiphenyls by measuring the concentration of polychlorobiphenyls in insulating oil comprises a step of, as pretreatment, bringing particles of a copolymer that contains divinylbenzene and a methacrylate organic monomer as monomer components into contact with insulating oil containing polychlorobiphenyls, so as to separate polychlorobiphenyls in insulating oil from oil content that is an impurity. The methacrylate organic monomer preferably has a diol type hydroxyl group.

4 Claims, 8 Drawing Sheets

(56) References Cited

OTHER PUBLICATIONS

Standard Method for Analysis of Polychlorinated Biphenyls (PCB) in Insulating Oil, Japan Electric Association Code (JEAC) 1201-1991.

Communication mailed Mar. 27, 2012, in connection with JP 2008-135013, 3 pages, Japanese Patent Office, Japan.

English translation of patentable claims of JP 2008-135013, 2 pages.

Claim Correspondence Table, 1 page.

Communication mailed Jun. 12, 2012, in connection with JP 2008-135013, 3 pages, Japanese Patent Office, Japan.

Ikegami et al., "Isolation of Polychlorodibenzo-p-dioxins and Polychlorobiphenyls upon Deproteinization of a Serum Sample by HPLC with Restricted-Access Reversed-Phase Packing Materials", J. High Resol. Chromatogr., 1999, pp. 287-293, vol. 22, Wiley-VCH.

Method for verifying disposal standards of specially controlled domestic waste and of specially controlled industrial waste, Announcement No. 192, Appendix 2, issued by the Ministry of Health and Welfare of Japan, published Jul. 3, 1992.

Yukio Noma, Analysis of small amount of PCB in insulating oil, Abstract of the $44^{th}$ and $45^{th}$ Meeting of the Japan Society for Environmental Chemistry, published Dec. 26, 2007.

Communication mailed Oct. 19, 2012, in connection with German Patent Application No. 11 2009 001 241.8, 6 pages, German Patent Office, Germany.

* cited by examiner

Recycle mode

PCB fractionation mode

PCB fractionation column concentration mode

Solvent removal mode

Thermal desorption mode

METHOD AND APPARATUS FOR ANALYSIS OF POLY (BIPHENYL CHLORIDE) IN ELECTRICAL INSULATING OIL

TECHNICAL FIELD

The present invention relates to a method for analyzing a sample that is separated from impurities with difficulty and requires highly sensitive analysis and an apparatus therefor. The present invention particularly relates to a method and an apparatus for conveniently analyzing with great accuracy polychlorobiphenyls (PCBs) in insulating oil.

BACKGROUND ART

In a PCB disposal facility, the reference level for determination of waste oil (treated oil and cleaning solution) after PCB treatment is 0.5 mg/kg. A concentration at the same level as or lower than this reference level indicates no contamination. A verification method therefor is disclosed in "Public Notice of the Ministry of Health and Welfare, No. 192 (appendix 2) of 1992" (Method 1, see Public Notice of the Ministry of Health and Welfare, No. 192 (appendix 2) of 1992), which comprises performing complicated pretreatment for removal of oil components that disturb analysis followed by analysis using a high resolution mass spectrometry.

Meanwhile, it has been revealed that insulating oil in heavy electric equipment such as a transformer (cylindrical transformer) contains trace amount(s) of PCBs. Hence, based on the Act on Special Measures concerning the Promotion of the Proper Treatment of PCB Waste, safe treatment of PCB-contaminated products, such as several million transformers stored in Japan, is required. A PCB concentration level in insulating oil that is the same as or lower than the reference level (0.5 mg/kg) requires no treatment. Accordingly, analysis for determining PCB concentration is important. However, the above verification method is conducted by manually performing complicated pretreatment involving a combination of solvent extraction, solid phase extraction, and sulfuric acid treatment, resulting in significant human error due to differences in degrees of proficiency. Moreover, it is difficult to secure measurement accuracy, and the method takes much time and effort, so that the analysis of several million specimens by such method has been unrealistic.

Meanwhile, various methods for more conveniently analyzing PCBs in insulating oil have been proposed. Examples of such methods include the "Method for Testing Polychlorobiphenyl (PCB) in Service Water•Drainage Water (JIS K0093-2002)" (Method 2, see Method for Testing Polychlorobiphenyl (PCB) in Service Water•Drainage Water (JIS K0093-2002)" (Revised Mar. 20, 2002)), "Japan Electric Association, Regulations concerning Methods for Analyzing Polychlorobiphenyl (PCB) in Insulating Oil (JEAC 1201-1991)" (Method 3; see Regulations concerning Methods for Analyzing Polychlorobiphenyl (PCB) in Insulating Oil (JEAC 1201-1991), Japan Electric Association" (Issued Sep. 30, 1991)), and "Institute of Petroleum Method" (Method 4; see Lecture Proceedings of $44^{th} \cdot 45^{th}$ Japan Society for Environmental Chemistry, 65-74, (Issued Dec. 26, 2007)). All of these methods comprise analyzing PCBs by gas chromatography with electron capture detector. Method 2 comprises performing alkaline degradation and then cleaning up a sample by column chromatography using a normal phase packing material such as silica gel or florisil. Method 3 comprises performing cleanup by sulfuric acid treatment via silica gel column chromatography and silica gel•florisil bi-layer column chromatography, wherein the lower limit of determination is about 2 mg/kg. Method 4 uses sulfuric acid treatment in combination since a correct result cannot be obtained by acetonitrile distribution and silica gel column chromatography alone.

In measurement of low-concentration PCBs in insulating oil, determination of the reference level of 0.5 mg/kg in waste oil is extremely difficult since the nature of PCBs closely resembles the nature of oil components. Examples of an analysis method that addresses such problem include a method (Method 5; see JP Patent Publication (Kokai) No. 2006-313125 A) that is a combination of the bi-layer column chromatography of Method 3 and sulfuric acid treatment and a method that involves extracting PCBs from insulating oil using a polar solvent (preferably, dimethyl sulfoxide) and then applying the polar solvent used for PCB extraction through a solid-phase extractor, so as to separate a PCB fraction (Method 6; see JP Patent Publication (Kokai) No. 2000-88825 A). Also, examples of a method that involves performing liquid chromatography instead of conventional column chromatography include a method that involves separating PCBs from waste oil by gel permeation chromatography using a polystyrene type absorbent based on a difference in molecular weight (Method 7) and a method that involves performing cleanup treatment and fractionation upon analysis of PCBs in environmental samples such as exhaust gas, ash, and drainage water resulting from waste treatment by liquid chromatography (Method 8; see JP Patent Publication (Kokai) No. 2001-83128 A). These methods are characterized by shortened treatment time, cleanup treatment with a small amount of a solvent, and being capable of continuously treating a plurality of samples. However, these methods are intended for environmental samples, so that no lower limit of determination for PCBs in insulating oil is presented.

DISCLOSURE OF THE INVENTION

Method 1 above is capable of analyzing a concentration of PCBs corresponding to the reference level (0.5 mg/kg) in insulating oil, but it requires about 2 days of pretreatment per specimen since the method takes much time for dimethyl sulfoxide distribution or sulfuric acid treatment and requires expensive analysis, since a high resolution mass spectrometry is used. Methods 2, 3, and 4 cannot completely remove insulating oil, and thus they result in insufficient sensitivity because of oil components as deterrents that are eluted simultaneously with PCBs upon measurement by gas chromatography. Cleanup that is performed in Method 5 by column chromatography is problematic in that: it requires a large amount of an elution solvent; it takes much time since a column for column chromatography must be prepared via wet packing for every measurement; and the performance of a packing material tends to change based on lot or state of preservation, so as to cause measurement errors. Also, treatment of multiple specimens requires many instruments and much equipment, but it does not allow automated treatment, and thus much time for treatment and effort are required. Solid-phase extraction that is performed in Method 6 is convenient since a commercial product previously packed with a packing material can be used. However, Method 6 requires the use of a large amount of a solvent for conditioning and PCB development, in addition to the confirmation of the elution capacity of PCBs and oil content every time a new lot is used in a solid-phase extraction column. Method 7 does not allow complete separation of oil content from PCBs and it does not allow analysis of low-concentration PCBs at the reference level or lower unless degradation treatment of oil components such as sulfuric acid treatment is employed in combination. Method 8 can be automated through the use of liquid chromatography, but the target in this method is an environmental sample, so that no lower limit of determination for PCBs in insulating oil is presented. Furthermore, cleanup methods using a sulfuric acid-impregnated silica gel column, a nitro column, and an activated carbon column are problematic in that the elimination of oil content is insufficient and sulfuric acid treatment or dimethyl sulfoxide distribution performed in the cleanup methods in Methods 1, 5, and 6 must be performed.

An object of the present invention is to address these conventional problems and thus to provide a method and an apparatus with which PCBs in insulating oil can be conveniently analyzed more rapidly at low cost and with higher accuracy.

Means to Solve the Problems

To achieve the above object, the present inventors have discovered that oil content can be efficiently separated from PCBs by bringing insulating oil containing polychlorobiphenyls (PCBs) into contact with microparticles comprising a copolymer that contains divinylbenzene and a methacrylate organic monomer as monomer components. Thus, the present inventors have completed the present invention.

The summary of the present invention is as follows.
(1) A method for analyzing polychlorobiphenyls by measuring the concentration of polychlorobiphenyls in insulating oil, comprising a step of, as pretreatment, bringing insulating oil containing polychlorobiphenyls into contact with particles of a copolymer that contains divinylbenzene and a methacrylate organic monomer as monomer components, so as to separate polychlorobiphenyls in insulating oil from oil content that is an impurity.
(2) The method for analyzing polychlorobiphenyls according to (1) above, wherein the methacrylate organic monomer has a diol type hydroxyl group or a group that can be converted to a diol type hydroxyl group.
(3) An analyzer for measuring the concentration of polychlorobiphenyls in insulating oil, which is provided with a vessel packed with particles of a copolymer that contains divinylbenzene and a methacrylate organic monomer as monomer components, wherein the vessel comprises:
a separation and refinement part for separating polychlorobiphenyls in insulating oil from oil content that is an impurity by causing the insulating oil containing the polychlorobiphenyls to pass through the vessel; and
an analytical part for measuring the concentration of polychlorobiphenyls in the insulating oil that has passed through the separation and refinement part.
(4) The analyzer for polychlorobiphenyls according to (3) above, wherein the methacrylate organic monomer has a diol type hydroxyl group or a group that can be converted to a diol type hydroxyl group.
(5) The analyzer for polychlorobiphenyls according to (3) or (4) above, wherein the vessel is a vessel for solid-phase extraction or a separation column to be used for a liquid chromatograph.
(6) The analyzer for polychlorobiphenyls according to any one of (3) to (5) above, wherein the vessel is a separation column to be used for a liquid chromatograph, is provided with a recycle valve for sending an eluent to the vessel via circulation, and is configured to recycle and send the solution until the oil content is sufficiently separated from the insulating oil.
(7) The analyzer for polychlorobiphenyls according to any one of (3) to (6) above, wherein the analytical part comprises a trap column for retaining polychlorobiphenyls and a 1st switching valve for fractionating and concentrating polychlorobiphenyls into the trap column, and a $2^{nd}$ switching valve for introducing polychlorobiphenyls into a gas chromatograph after desorption of the polychlorobiphenyls from the trap column.
(8) The analyzer for polychlorobiphenyls according to (7) above, by which a helium gas is run through a trap column so as to remove the eluent and water content remaining in the trap column.

Effect of the Invention

Conventionally, pretreatment such as solvent extraction, column chromatography, solid-phase extraction, or the like has been performed by hand. However, in measurement of low concentration PCBs in insulating oil, separation of PCBs from oil content has been difficult, since they closely resemble each other in nature. According to the present invention, an organic polymer-based pretreatment agent having a specific nature is used, a solid-phase extraction column or a separation column for a liquid chromatograph is packed with the pretreatment agent, and then cleanup of insulating oil is performed using these columns. Thus, in addition to sulfuric acid treatment, which previously has been required, becoming unnecessary, automation is also facilitated. Specifically, the present invention is convenient since no manual operation is required. Moreover, the present invention enables labor saving, since it requires no glass instruments or equipment that has been used in large quantities. Also, the use of an autosampler for a liquid chromatograph enables automated and unmanned treatment of multiple specimens. Moreover, automation results in no human error due to different degrees of proficiency, thereby improving analytical precision.

A column packed with particles of a copolymer of divinylbenzene and a methacrylate organic polymer having a diol type hydroxyl group as a functional group is used as a cleanup column, thereby lowering the amount of a solvent to be used in conventional column chromatography, solid-phase extraction, or gel permeation chromatography. Also, no other reagents or packing materials, solid-phase columns, or the like are used, resulting in inexpensive analysis cost.

The use of a thermal desorption apparatus comprising a trap column and switching valves enables automation of concentration procedures. Thus, a step involving concentration procedures conducted by hand using a rotary evaporator can be skipped, so that all steps can be automatically performed. Analysis takes about 2 days per specimen according to the official method. The time for the same analysis can be shortened to 2 to 3 hours per specimen according to the present invention, while similar analytical precision can be achieved. Moreover, safety is high since no dangerous reagent such as concentrated sulfuric acid or an alkaline solution is used. Good results can be obtained by even a person who is not a skilled analyst.

This description includes part or all of the contents as disclosed in the description and/or drawings of Japanese Patent Application No. 2008-135013, which is a priority document of the present application.

DESCRIPTION OF SYMBOLS

Figure 1:
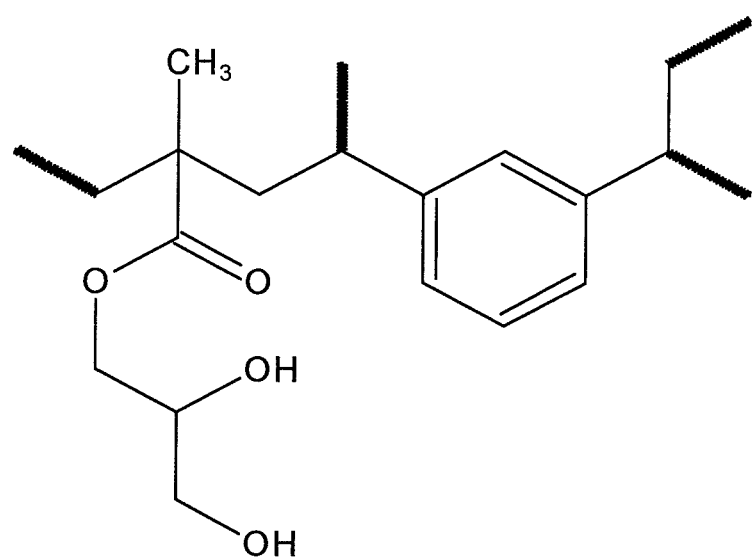
FIG. 1 shows the molecular structure of a copolymer to be used for pretreatment, which contains divinylbenzene and a methacrylate organic monomer having a diol type hydroxyl group as monomer components.

1 . . . Screw-type column end
2 . . . Pipe
3 . . . Pretreatment agent
4 . . . Filter
5 . . . Threaded hole for tube connection
6 . . . Eluent
7 . . . Recycle valve
8 . . . Pump
9 . . . Autosampler
10 . . . Cleanup column
11 . . . Detector for determination of separation
12 . . . Control part for recycle valve
13 . . . Fraction collector
14 . . . Thermal desorption apparatus
15 . . . GC/MS apparatus
16 . . . Liquid chromatograph with recycling function
17 . . . Six-way valve
18 . . . Four-way valve
19 . . . Trap column

DESCRIPTION OF THE PREFERRED
EMBODIMENTS OF THE INVENTION

The present invention will be explained more specifically as follows.

The method for analyzing polychlorobiphenyls of the present invention, and specifically, the method for measuring the concentration of polychlorobiphenyls in insulating oil of the present invention, is characterized by comprising, as pretreatment, a step of bringing particles of a copolymer that contains divinylbenzene and a methacrylate organic monomer as monomer components into contact with insulating oil containing polychlorobiphenyls, so as to separate polychlorobiphenyls in insulating oil from oil content that is an impurity. As forms of insulating oil, those used for electric power devices such as cylindrical transformers and suspected of containing trace amounts of polychlorobiphenyls may be subjected to analysis. Here, the term "polychlorobiphenyls" or "PCBs" refers to compounds that are represented by the general formula $C_{12}H_nCl_{10-n}$ ($0 \leq n \leq 9$) (wherein a hydrogen atom of biphenyl is substituted with a chlorine atom) and include all isomers resulting from differences in the number or position of chlorine substituted.

Upon analysis, insulating oil may be diluted in advance and then used if necessary. Also, in some cases, oil content becomes degraded by sulfuric acid treatment and then separation may be performed using the above copolymer particles.

As a methacrylate organic monomer, methacrylate having a substitution with a group or the like that can be converted to an amino group, a hydroxy group, or a diol type hydroxyl group, in addition to alkyl methacrylate such as methyl methacrylate and ethyl methacrylate, can be used. In particular, the above copolymer having a diol type hydroxyl group is preferably used since it has good ability to separate from PCBs. Here, when a diol type hydroxyl group is alkyl methacrylate, the alcohol portion is preferably a 2,3-diol type. FIG. 1 shows an example of the molecular structure of such a copolymer. FIG. 1 shows a copolymer of 2,3-dihydroxy propyl methacrylate (glycerol monomethacrylate) and divinylbenzene, wherein thick lines indicate bonds with other monomer units or cross-links with other molecular chains. The copolymer ratio of divinylbenzene to a methacrylate organic monomer is not particularly limited. In general, the proportion of divinylbenzene to the entire copolymer (1) in terms of molar ratio ranges from about 0.2:1 to 0.8:1. Also, in some cases, monomers other than divinylbenzene and a methacrylate organic monomer may also be contained as constitutional units. Examples of such 3rd monomer components include styrene and an organic monomer having two or more double bonds. The 3rd monomer component in a copolymer preferably accounts for less than 10% of the copolymer in terms of molar ratio. An example of a packing material comprising copolymer particles having the structure in FIG. 1 is the NOBIAS RP-SG1 column packing material (trade name, Hitachi High-Technologies Corporation).

Regarding the particle diameter of copolymer particles, copolymer particles with a particle diameter ranging from 3 μm to 100 μm can be used in a manner similar to that used with a general solid-phase extraction column or separation column for a liquid chromatograph. The particle diameter desirably ranges from about 5 μm to 50 μm. In particular, employment of a micro-particle diameter of 10 μm or less enables efficient separation and refinement of insulating oil. Also, the porosity of particles is not limited, but particles preferably have a specific surface area ranging from about 100 $m^2$/g to about 500 $m^2$/g and a pore size ranging from about 10 angstroms to about 1000 angstroms, as determined by gas adsorption.

A pretreatment agent comprising the copolymer particles is generally contained in a vessel having chemically and mechanically sufficient strength. A column packed with a pretreatment agent is used for liquid chromatography with a recycling function, so that separation and refinement of insulating oil can be performed even more effectively. Also, introduction of insulating oil samples is performed automatically using an autosampler, so that multiple specimens can be continuously treated in a fully automatic manner.

Oil content that is an impurity cannot be completely removed by conventional methods. However, through the use of a cleanup column packed with, as a pretreatment agent, particles of a copolymer of methacrylate having a diol type hydroxyl group as a functional group and divinylbenzene having a phenyl group, oil content can be more effectively separated from PCBs compared with cleanup performed via column chromatography using sulfuric acid-impregnated silica gel, florisil, or the like as a packing material, solid-phase extraction, or gel permeation chromatography using a polystyrene packing material. Furthermore, through the use of a liquid chromatograph with a recycling function, insulating oil can be caused to pass several times through a cleanup column, so that oil content can be completely removed from PCB-contaminated insulating oil. In addition, the number of instances of recycling can be varied depending on the type of insulating oil and the like.

After cleanup, PCB fractions are collected and concentration treatment is performed. These procedures are automated using a trap column having a thermal desorption function, so that the total amount of PCBs in an insulating oil sample can be fractionated (collected), concentrated, and then measured. Hence, the resulting sensitivity is several-hundred-fold higher than those of manual methods. Upon measurement, introduction of an eluent or water into a gas chromatograph may disturb the measurement. A helium gas is caused to pass through a trap column before thermal desorption targeting PCBs to remove them, making it possible to perform analysis with an even higher degree of precision.

PCB fractions can be collected using a fraction collector. However, in this case, the total amount of PCBs in a sample cannot be injected into a gas chromatograph.

EXAMPLES

Next, the Examples of the present invention are as described below based on the drawings.

Example 1

Figure 2:
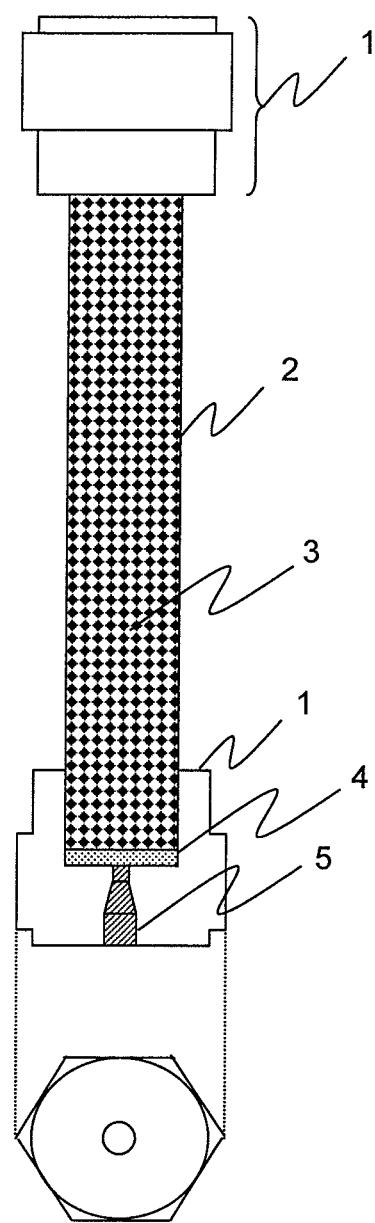
FIG. 2 is a schematic view showing the configuration of a column packed with a pretreatment agent in Example 1.

FIG. 2 shows a column packed with a pretreatment agent comprising particles of a copolymer that contains divinylbenzene and a methacrylate organic polymer. Both ends of a pipe 2 are sealed with a screw-type column end 1, so that a pretreatment agent 3 packing the pipe 2 is locked therein so as not to form any empty space. When particles are mixed as impurities within an insulating oil sample, filters 4 are used for the both ends of the pipe 2, so as to prevent the particles from being mixed in the layer of the pretreatment agent 3. Meanwhile, a liquid enters the pretreatment agent 3 via a threaded hole for tube connection 5, which is produced for connection to a liquid chromatograph.

Figure 3:
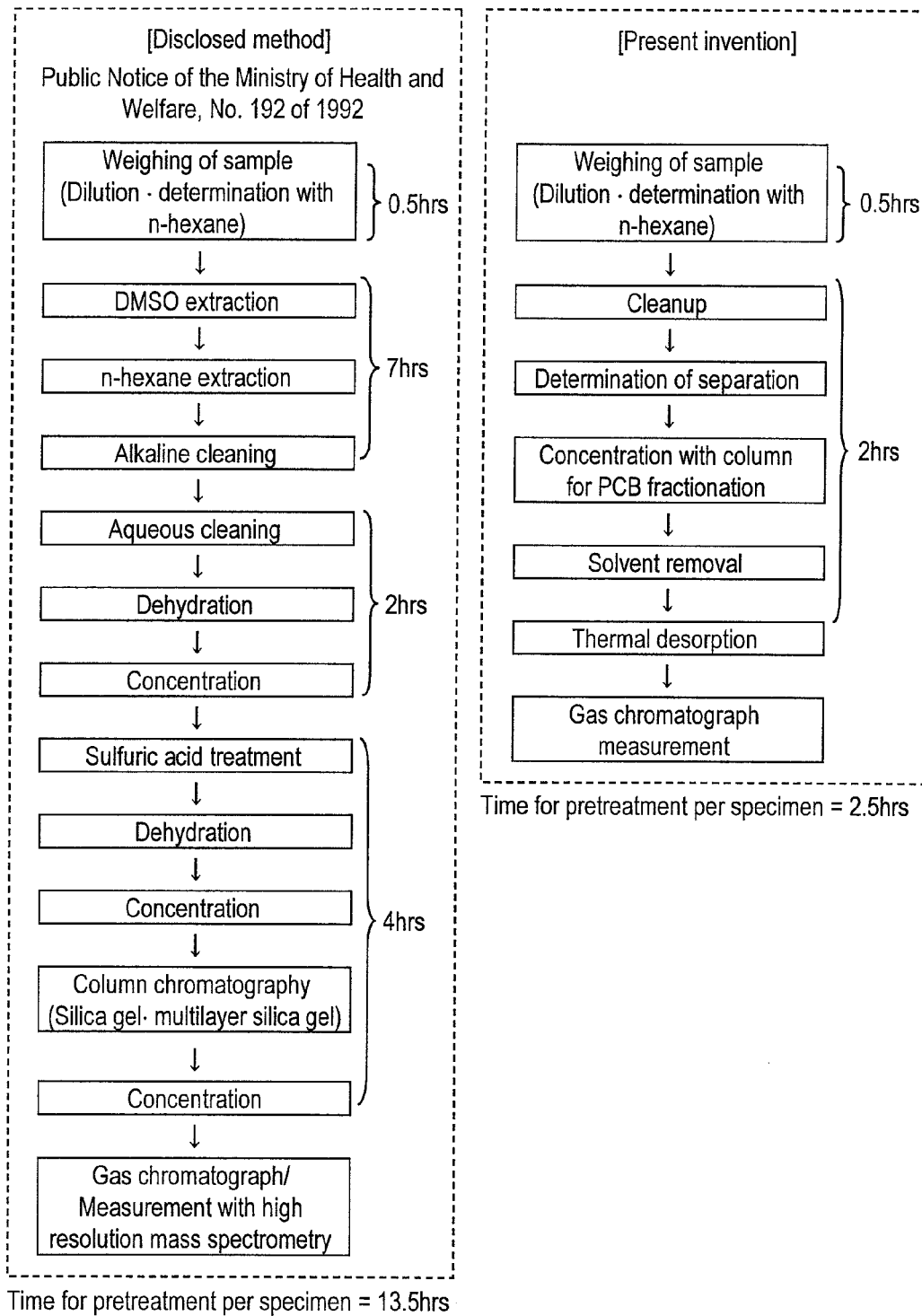
FIG. 3 is an operational flow chart for analyzing PCBs in insulating oil.

FIG. 3 shows an operational flow chart for analyzing PCBs in insulating oil, whereby the operational flow chart of the present invention is compared with that of the disclosed method. The disclosed method is the sole method by which PCBs (in waste oil) at the same level as or lower than the reference level (0.5 mg/kg) to be analyzed with high accuracy. When they are compared in terms of the time for pretreatment, the disclosed method takes 13.5 hours (about 2 days) while the automatic pretreatment method according to the present invention takes 2.5 hours.

Figure 4:
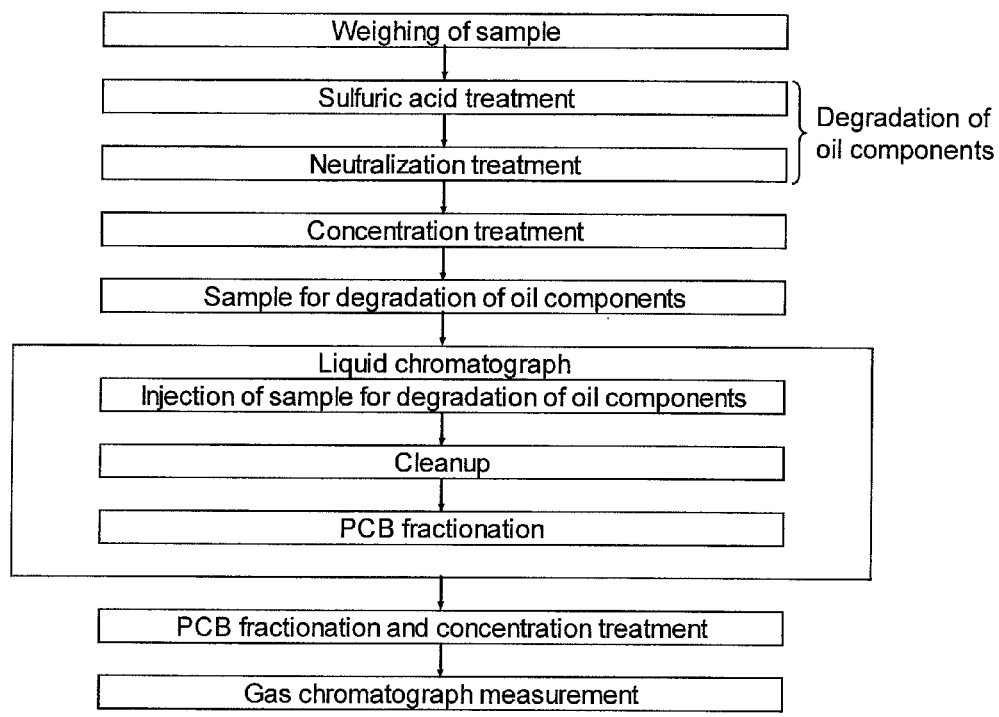
FIG. 4 is an operational flow chart for analyzing PCBs when degradation treatment of oil components and concentration treatment are performed by manual operation in Example 1.
Figure 5:
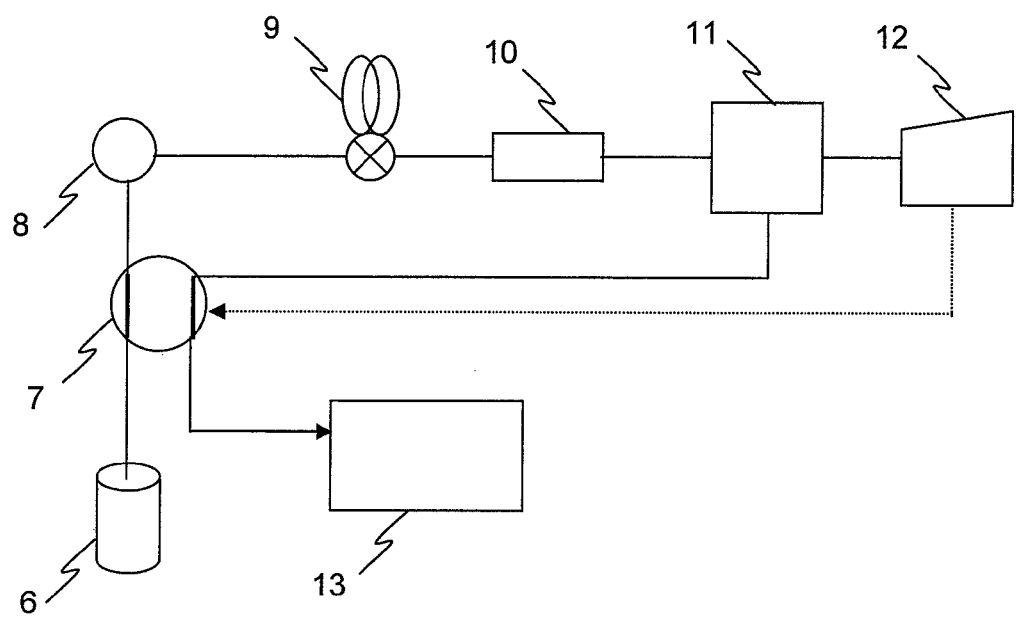
FIG. 5 is a schematic view showing the configuration of an analyzer for PCBs in insulating oil in Example 1.

FIG. 4 shows the operational flow chart for analyzing PCBs in insulating oil as in the Examples. This analytical method involves manually performing the steps of degradation and concentration treatment of oil components upon analysis of PCBs in insulating oil and then automatically performing a cleanup step for separating PCBs in insulating oil from oil content that is an impurity. As in the Examples, it is preferable to perform degradation treatment using sulfuric acid prior to the cleanup step, so as to lower the concentration of oil content in insulating oil. As described above, sulfuric acid treatment may be skipped in the present invention, if necessary, unlike the conventional techniques that require sulfuric acid treatment. FIG. 5 is a schematic view showing a liquid chromatograph for performing cleanup.

First, degradation treatment of oil components, which is performed via manual operation, is as described below. Sulfuric acid treatment is performed by weighing and adding to a 100-ml separatory funnel 0.1 g of an insulating oil sample, 10 ml of n-hexane, and 25 ml of concentrated sulfuric acid, shaking the funnel for 10 minutes, and leaving it to stand for 20 minutes for separation and partitioning. This is performed twice, so that an n-hexane layer is fractionated. Neutralization treatment is performed by adding a basic solution such as a potassium hydroxide solution or a sodium hydroxide solution, so as to neutralize the resultant to pH 6-8. The resultant is concentrated to 1 ml using a rotary evaporator, a nitrogen gas purge, or the like, so that a sample is prepared for degradation treatment of oil components.

Next, cleanup treatment is performed automatically with a liquid chromatograph. Specifically, first, a predetermined amount of a sample for degradation treatment of oil components is injected using an autosampler 9 as shown in FIG. 5. The injected sample is sent to a cleanup column (separation column) 10 with an eluent 6 that is sent by a pump 8, and then impurities such as oil content are separated from PCBs, so that cleanup treatment is performed. Since degradation treatment of oil components is performed in advance, cleanup treatment is completed with a single separation. N-hexane or the like is used as an eluent.

A method for PCB fractionation and collection is performed as follows. Cleanup conditions are set in advance for a liquid chromatograph (to be used herein) using a standard PCB sample, and the elution time for a PCB fraction is also confirmed in advance. Next, the sample for degradation treatment of oil components is injected into the liquid chromatograph, a valve for a fraction collector 13 is switched at the time of elution of the PCB fraction in the sample, and then the PCB fraction is collected. The thus obtained PCB fraction is concentrated to 0.5 ml using a rotary evaporator, a nitrogen gas purge, or the like. The resultant (1-2 μl) is injected into a GC/MS (or GC/ECD) apparatus 15 and then measured.

Example 2

Figure 6:
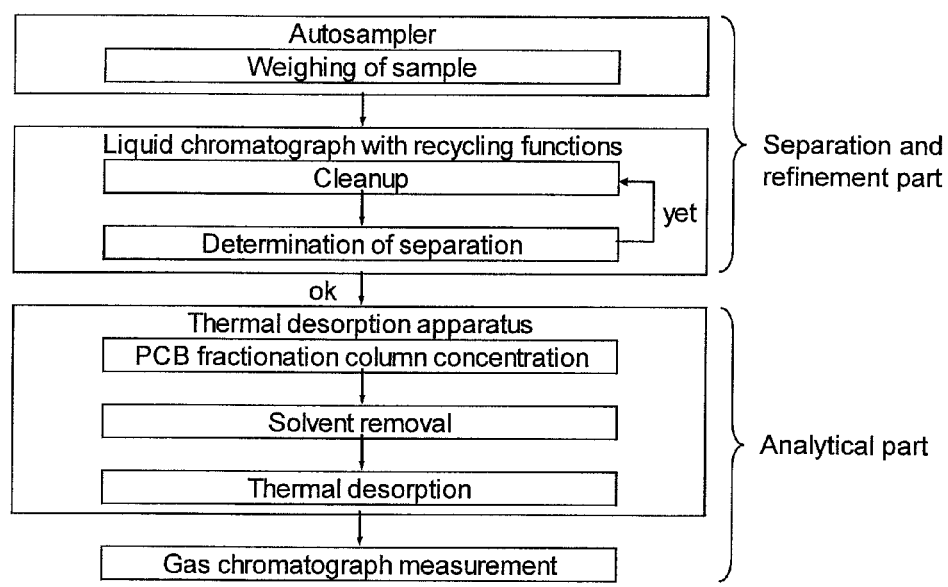
FIG. 6 is an operational flow chart showing a situation in which all steps for analyzing PCBs in insulating oil are performed automatically in Example 2.
Figure 7:
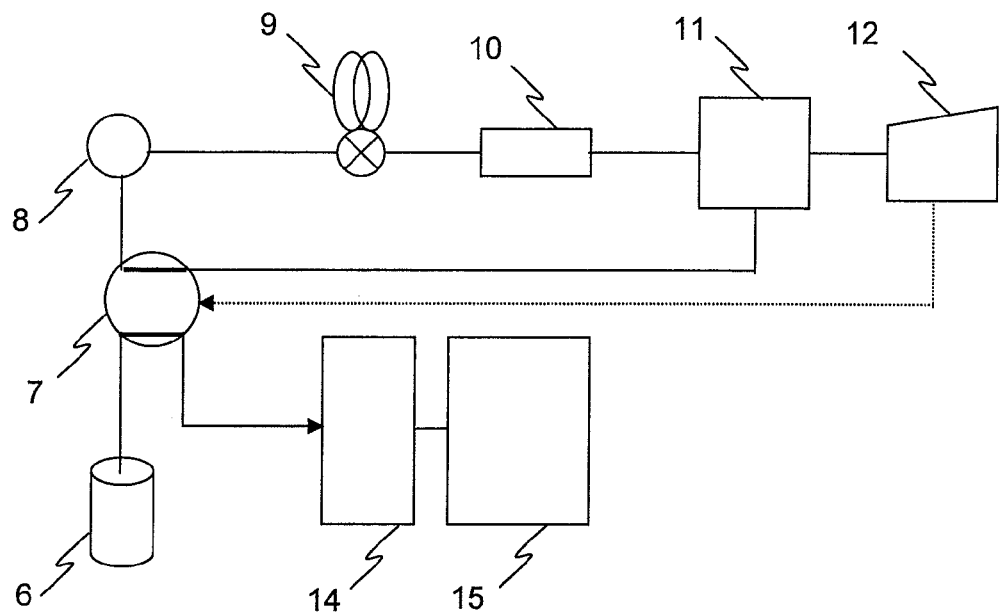
FIG. 7 is a schematic view showing a separation and refinement part of an analyzer for PCBs in insulating oil in Example 2.
Figure 7:
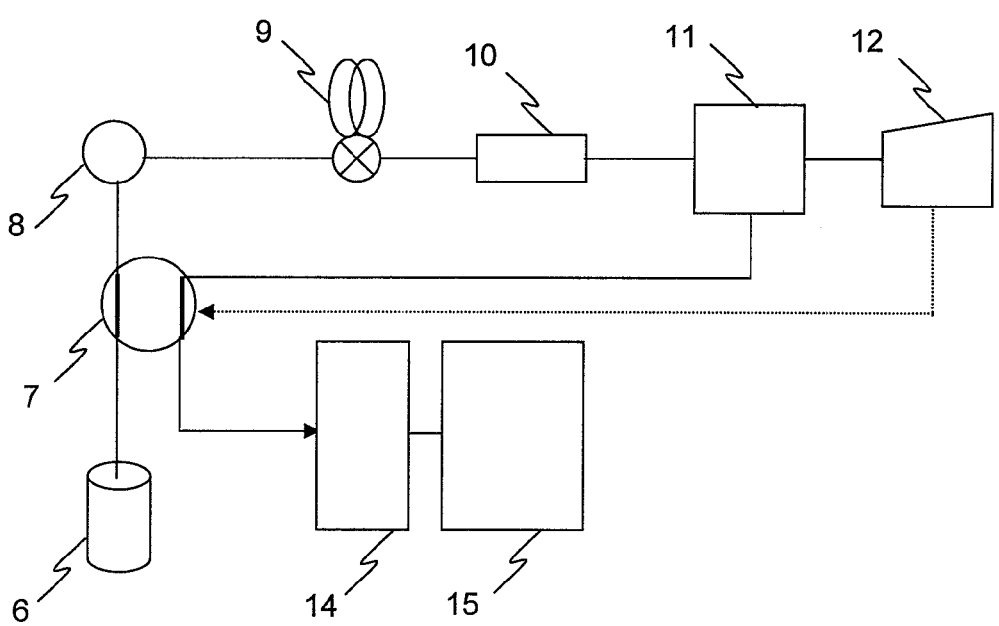
Figure 8:
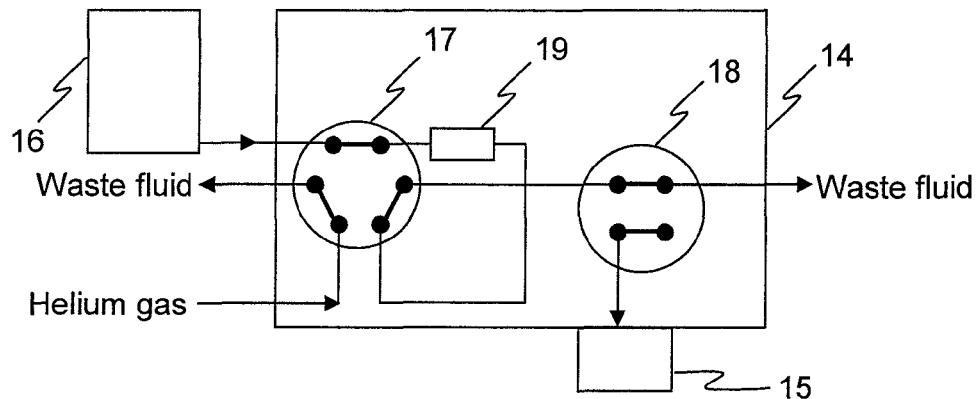
FIG. 8 is a schematic view showing an analytical part of an analyzer for PCBs in insulating oil in Example 2.
Figure 8:
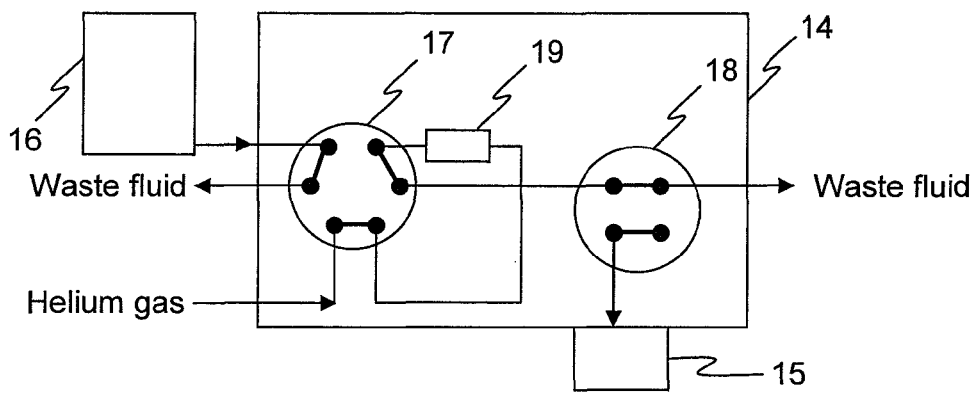
Figure 8:
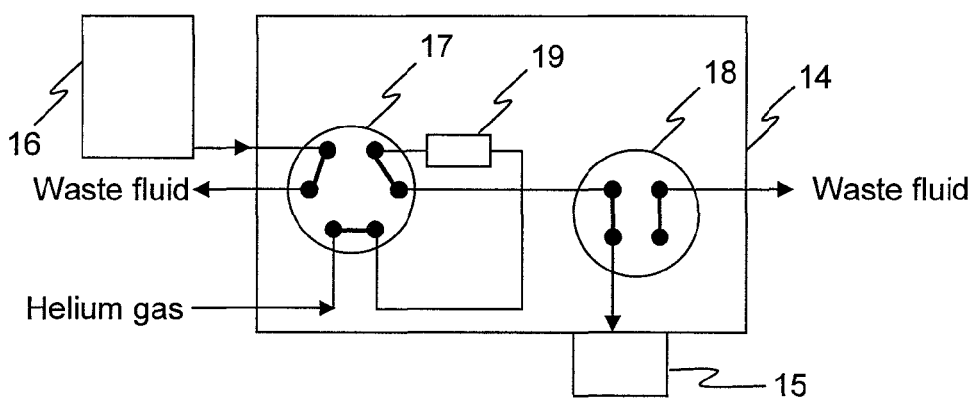

FIG. 6 shows an operational flow chart for analyzing PCBs in insulating oil in Example 2. In this Example, degradation treatment of oil components and concentration treatment are not performed prior to cleanup, but all steps ranging from weighing of an insulating oil sample to measurement with a gas chromatograph are performed automatically. FIG. 7 is a schematic view showing the configuration of an analyzer for PCBs in insulating oil for such automatic procedures. In particular, FIG. 7 shows a separation and refinement part for separation of PCBs in insulating oil from oil content. FIG. 8 is a schematic view showing the configuration of an analytical part of an analyzer for PCBs in insulating oil and particularly showing an analytical part for measurement of PCB concentration in insulating oil that has passed through the separation and refinement part.

0.1 g of an insulating oil sample diluted with n-hexane is injected using the autosampler 9 into a liquid chromatograph with a recycling function. The injected sample is sent to the cleanup column (separation column) 10 with the eluent 6 sent by a pump 8, and then impurities such as oil content are separated from PCBs, so that cleanup treatment is performed. An apparatus for determination of separation 11 is placed immediately adjacent to the cleanup column 10. Determination is performed using a ultraviolet visible detector (UV) or a diode array detector (DAD). Specifically, the separation (behavior) of impurities (oil content) from PCBs is monitored. If separation of impurities from PCBs is insufficient, the recycle valve 7 is switched by the control part for recycle valve 12, so as to switch back the flow path to the cleanup column 10 (recycle mode). If separation is sufficient, the flow path of the recycle valve 7 is switched by the control part for recycle valve 12 to a thermal desorption apparatus 14 corresponding to an analytical part (PCB fraction collection mode). Determination of separation is performed by subjecting a chromatogram detected by the detector to waveform processing and then calculating the degree of peak separation with respect to a chromatogram obtained in advance from the standard PCB sample. Criteria for the degree of separation are provided, so that it is automatically determined whether further recycling should be performed.

In a thermal desorption apparatus 14 in FIG. 8, a six-way valve 17 that is a first switching valve is connected to a trap column 19 and then a PCB fraction is concentrated in a trap column 19 (PCB fraction column concentration mode). For collection of the PCB fraction, the capacity for elution of PCBs per instance of recycling should be confirmed in advance with the use of a standard sample. Next, the six-way valve 17 is switched and then helium gas is run into the trap column 19. At this time, the trap column is heated to a temperature higher by about 10° C. than the boiling point of the eluent. Thus, the eluent of recycle LC remaining in the trap column and water in the sample can be removed (solvent removal mode). At this time, it is required to set a temperature at which components (of PCB isomers) having low boiling points are not desorbed from the trap column 19. Subsequently, the trap column 19 is heated without stopping to a temperature (about 250° C.-300° C.) at which trapped PCBs are desorbed and then PCBs are sent to a GC/MS (or GC/ECD) apparatus 15 as a detection part and then measured (thermal desorption mode).

Example 3

As another example, a method for performing cleanup without using a liquid chromatograph is as described below. A pretreatment agent comprising particles of a copolymer that contains divinylbenzene and a methacrylate organic monomer as monomer components is added together with an appropriate solvent into a glass vessel such as a beaker. An insulating oil sample is added to such a vessel and then stirred for a certain time at a certain temperature, so that only PCBs in the sample are retained in the pretreatment agent. Then the pretreatment agent is separated by filtration and treated with a solvent for desorption of PCBs from the pretreatment agent, so that PCBs are recovered and measured, or PCBs are recovered by heating and then measured.

Alternatively, a glass tube is packed with a pretreatment agent and then insulating oil is retained therewithin. A fiber surface is coated with the pretreatment agent and then immersed in the insulating oil, so that PCBs in the insulating oil are retained by the pretreatment agent. Subsequently, the pretreatment agent retaining the PCBs is caused to pass through a solvent or inserted into an inlet of a gas chromatograph and then heated. In such manner, PCBs can be desorbed from the pretreatment agent and then measured.

All publications, patents, and patent applications cited herein are incorporated herein by reference in their entirety.

The invention claimed is:

1. An analyzer for measuring the concentration of polychlorobiphenyls in insulating oil, the analyzer comprising:
    a separation and refinement part for separating polychlorobiphenyls in insulating oil from oil content that is an impurity; and
    an analytical part for measuring the concentration of polychlorobiphenyls in the insulating oil that has passed through the separation and refinement part,
    wherein the separation and refinement part comprises a sample injection part for injecting insulating oil containing polychlorobiphenyls, a vessel for causing the injected insulating oil to be passed through and a detector for determination of separation for determining whether or not separation of polychlorobiphenyls in the passed through insulating oil from oil content that is an impurity is sufficient,
    wherein the vessel is packed with particles of a copolymer that contains divinylbenzene and a methacrylate organic monomer having a diol hydroxyl group as monomer components;
    wherein the analytical part comprises a trap column for retaining polychlorophenyls, a 1st switching valve for fractionating and concentrating polychlorophenyls into the trap column, and a 2nd switching valve for introducing polychlorophenyls into a gas chromatograph after desorption of the polychlorophenyls from the trap column.

2. The analyzer for polychlorobiphenyls according to claim 1, wherein the vessel is a vessel for solid-phase extraction or a separation column to be used for a liquid chromatograph.

3. The analyzer for polychlorobiphenyls according to claim 2, wherein the vessel is a separation column to be used for a liquid chromatograph, is provided with a recycle valve for sending an eluent to the vessel via circulation, and is configured to recycle and send the solution until the oil content is sufficiently separated from the insulating oil.

4. The analyzer for polychlorobiphenyls according to claim 1, wherein a helium gas is run through the trap column to remove the eluent and water remaining in the trap column.

* * * * *